US010316465B2

(12) United States Patent
Monclin

(10) Patent No.: US 10,316,465 B2
(45) Date of Patent: Jun. 11, 2019

(54) PROCESS AND APPARATUS FOR BIOMASS CLEANING IN LIGNOCELLULOSIC BIOREFINERIES

(71) Applicant: API Intellectual Property Holdings, LLC, Atlanta, GA (US)

(72) Inventor: Jean-Pierre Monclin, Atlanta, GA (US)

(73) Assignee: GranBio Intellectual Property Holdings, LLC, Atlanta, GA (US)

( * ) Notice: Subject to any disclaimer, the term of this patent is extended or adjusted under 35 U.S.C. 154(b) by 577 days.

(21) Appl. No.: 14/944,861

(22) Filed: Nov. 18, 2015

(65) Prior Publication Data

US 2016/0138218 A1 May 19, 2016

Related U.S. Application Data

(60) Provisional application No. 62/082,105, filed on Nov. 19, 2014, provisional application No. 62/085,641, filed on Nov. 30, 2014.

(51) Int. Cl.
*D21B 1/02* (2006.01)
*C13K 1/02* (2006.01)
*C08H 8/00* (2010.01)

(52) U.S. Cl.
CPC ............ *D21B 1/023* (2013.01); *C08H 8/00* (2013.01); *C13K 1/02* (2013.01); *D21B 1/02* (2013.01)

(58) Field of Classification Search
CPC .................................. D21B 1/023; D21B 1/02
See application file for complete search history.

(56) References Cited

U.S. PATENT DOCUMENTS

| 3,081,218 | A | * | 3/1963 | Ambuehl | D21C 3/24 162/19 |
| 4,050,980 | A | * | 9/1977 | Schmidt | D21B 1/02 162/24 |
| 4,376,042 | A | * | 3/1983 | Brown | D21B 1/023 209/2 |
| 5,298,119 | A | * | 3/1994 | Brown | B07B 1/15 162/55 |
| 6,283,300 | B1 | * | 9/2001 | Bielagus | B07B 4/02 209/139.1 |

(Continued)

*Primary Examiner* — Anthony Calandra
(74) *Attorney, Agent, or Firm* — O'Connor & Company; Ryan P. O'Connor

(57) ABSTRACT

A wet process for cleaning biomass is disclosed, comprising: introducing biomass feedstock to a vibrating separator, to generate an overflow stream and an underflow stream, wherein the overflow stream comprises biomass and large grit, and wherein the underflow stream comprises fines and small grit; introducing the overflow stream to a kinetic separator, to generate an intermediate biomass stream and a large-grit stream; introducing the underflow stream and elutriation water to a hydroclone separator, to generate a wet biomass-fines stream and a small-grit stream; separating water contained in the wet biomass-fines stream and recycling it as elutriation water, to generate a biomass fines stream; and combining the biomass fines stream with the intermediate biomass stream, thereby generating clean biomass. An alternative embodiment for a dry process to clean biomass is also disclosed. The clean biomass may be used in a wide variety of biorefining processes.

12 Claims, 2 Drawing Sheets

(56) References Cited

U.S. PATENT DOCUMENTS

| | | | |
|---|---|---|---|
| 9,562,322 B1* | 2/2017 | Post | D21B 1/026 |
| 2007/0095728 A1* | 5/2007 | Ottow | B07B 4/02 |
| | | | 209/714 |
| 2010/0287826 A1* | 11/2010 | Hoffman | C10L 5/363 |
| | | | 44/605 |
| 2013/0200181 A1* | 8/2013 | Lanning | B03B 9/06 |
| | | | 241/24.1 |
| 2014/0299684 A1* | 10/2014 | Shideler, Jr. | B02C 23/14 |
| | | | 241/19 |

* cited by examiner

PROCESS AND APPARATUS FOR BIOMASS CLEANING IN LIGNOCELLULOSIC BIOREFINERIES

PRIORITY DATA

This patent application is a non-provisional application claiming priority to U.S. Provisional Patent App. No. 62/082,105, filed Nov. 19, 2014, and to U.S. Provisional Patent App. No. 62/085,641, filed Nov. 30, 2014, each of which is hereby incorporated by reference herein.

FIELD

The present invention generally relates to biomass cleaning prior to converting biomass into fermentable sugars, cellulose, and lignin.

BACKGROUND

Biomass refining (or biorefining) is becoming more prevalent in industry. Cellulose fibers and sugars, hemicellulose sugars, lignin, syngas, and derivatives of these intermediates are being used by many companies for chemical and fuel production. Indeed, we now are observing the commercialization of integrated biorefineries that are capable of processing incoming biomass much the same as petroleum refineries now process crude oil. Underutilized lignocellulosic biomass feedstocks have the potential to be much cheaper than petroleum, on a carbon basis, as well as much better from an environmental life-cycle standpoint.

Lignocellulosic biomass is the most abundant renewable material on the planet and has long been recognized as a potential feedstock for producing chemicals, fuels, and materials. Lignocellulosic biomass normally comprises primarily cellulose, hemicellulose, and lignin. Cellulose and hemicellulose are natural polymers of sugars, and lignin is an aromatic/aliphatic hydrocarbon polymer reinforcing the entire biomass network. Some forms of biomass (e.g., recycled materials) do not contain hemicellulose.

There are many reasons why it would be beneficial to process biomass in a way that effectively separates the major fractions (cellulose, hemicellulose, and lignin) from each other. Cellulose from biomass can be used in industrial cellulose applications directly, such as to make paper or other pulp-derived products. The cellulose can also be subjected to further processing to either modify the cellulose in some way or convert it into glucose. Hemicellulose sugars can be fermented to a variety of products, such as ethanol, or converted to other chemicals. Lignin from biomass has value as a solid fuel and also as an energy feedstock to produce liquid fuels, synthesis gas, or hydrogen; and as an intermediate to make a variety of polymeric compounds. Additionally, minor components such as proteins or rare sugars can be extracted and purified for specialty applications.

In light of this objective, a major shortcoming of previous process technologies is that one or two of the major components can be economically recovered in high yields, but not all three. Either the third component is sacrificially degraded in an effort to produce the other two components, or incomplete fractionation is accomplished. An important example is traditional biomass pulping (to produce paper and related goods). Cellulose is recovered in high yields, but lignin is primarily consumed by oxidation and hemicellulose sugars are mostly degraded. Approximately half of the starting biomass is essentially wasted in this manufacturing process. State-of-the-art biomass-pretreatment approaches typically can produce high yields of hemicellulose sugars but suffer from moderate cellulose and lignin yields.

There are several possible pathways to convert biomass into intermediates. One thermochemical pathway converts the feedstock into syngas (CO and $H_2$) through gasification or partial oxidation. Another thermochemical pathway converts biomass into liquid bio-oils through pyrolysis and separation. These are both high-temperature processes that intentionally destroy sugars in biomass.

Sugars (e.g., glucose and xylose) are desirable platform molecules because they can be fermented to a wide variety of fuels and chemicals, used to grow organisms or produce enzymes, converted catalytically to chemicals, or recovered and sold to the market. To recover sugars from biomass, the cellulose and/or the hemicellulose in the biomass must be hydrolyzed into sugars. This is a difficult task because lignin and hemicelluloses are bound to each other by covalent bonds, and the three components are arranged inside the fiber wall in a complex manner. This recalcitrance explains the natural resistance of woody biomass to decomposition, and explains the difficulty to convert biomass to sugars at high yields.

Fractionation of biomass into its principle components (cellulose, hemicellulose, and lignin) has several advantages. Fractionation of lignocellulosics leads to release of cellulosic fibers and opens the cell wall structure by dissolution of lignin and hemicellulose between the cellulose microfibrils. The fibers become more accessible for hydrolysis by enzymes. When the sugars in lignocellulosics are used as feedstock for fermentation, the process to open up the cell wall structure is often called "pretreatment." Pretreatment can significantly impact the production cost of lignocellulosic ethanol.

Many types of pretreatment have been studied. A common chemical pretreatment process employs a dilute acid, usually sulfuric acid, to hydrolyze and extract hemicellulose sugars and some lignin. A common physical pretreatment process employs steam explosion to mechanically disrupt the cellulose fibers and promote some separation of hemicellulose and lignin. Combinations of chemical and physical pretreatments are possible, such as acid pretreatment coupled with mechanical refining. It is difficult to avoid degradation of sugars. In some cases, severe pretreatments (i.e., high temperature and/or low pH) intentionally dehydrate sugars to furfural, levulinic acid, and related chemicals. Also, in common acidic pretreatment approaches, lignin handling is very problematic because acid-condensed lignin precipitates and forms deposits on surfaces throughout the process.

Contrary to traditional fossil fuel feedstocks (oil, natural gas, and coal), or even first-generation crop or lignocellulosic biomass feedstocks (corn, sugarcane, wood, etc.), agricultural residues such as sugarcane bagasse and straw, corn stover, wheat straw, and the like pose significant challenges at the front end of a biorefinery. In particular, these agricultural-residue feedstocks typically have high dirt, ash, and mineral content. Such components can cause mechanical erosion in the plant, among other problems. Also, lignocellulosic feedstocks are very susceptible to the formation of fines and pith which can cause processing problems and/or reduced yields of desired products. Improvements are desired for biomass cleaning.

SUMMARY

The present invention addresses the aforementioned needs in the art.

In some variations, the invention provides a wet process for cleaning biomass, the process comprising:

(a) providing biomass feedstock;
(b) introducing the feedstock to a vibrating separator, to generate an overflow stream and an underflow stream, wherein the overflow stream comprises biomass and large grit, and wherein the underflow stream comprises fines and small grit;
(c) introducing at least a portion of the overflow stream to a kinetic separator, to generate an intermediate biomass stream and a large-grit stream;
(d) introducing at least a portion of the underflow stream and elutriation water to a hydrocyclone separator, to generate a wet biomass-fines stream and a small-grit stream;
(e) separating at least some water contained in the wet biomass-fines stream and recycling the water to step (d) as at least some of the elutriation water, to generate a biomass fines stream; and
(f) combining at least some of the biomass fines stream with the intermediate biomass stream from step (c), thereby generating clean biomass.

In some embodiments, the biomass feedstock is (or includes) lignocellulosic biomass. For example, the lignocellulosic biomass may be selected from the group consisting of sugarcane bagasse, sugarcane straw, energy cane bagasse, energy cane straw, corn stover, corn fiber, wheat straw, rice straw, oat straw, barley straw, miscanthus, and combinations thereof.

The clean biomass preferably contains at least 90%, 91%, 92%, 93%, 94%, 95%, 96%, 97%, 98%, or 99% of the biomass content in the biomass feedstock. The process preferably removes at least 90%, 91%, 92%, 93%, 94%, 95%, 96%, 97%, 98%, 99%, 99.5% or more of the grit contained in the biomass feedstock.

Relatively low amounts of fresh water are necessary in step (d), since water is recycled from step (e) to function as elutriation water. In some embodiments, the process utilizes about or less than about 900, 800, 700, 600, 500, 400, 300, 250, 200, 150, 100, 90, 80, 70, 60, or 50 gallons of make-up water as elutriation water in step (d).

In other variations of the invention, a dry process for cleaning biomass comprises:

(a) providing biomass feedstock;
(b) introducing the feedstock to a first vibrating separator, to generate a first overflow stream and a first underflow stream, wherein the first overflow stream comprises biomass and large grit, and wherein the first underflow stream comprises fines and small grit;
(c) introducing at least a portion of the first overflow stream to a kinetic separator, to generate an intermediate biomass stream and a large-grit stream;
(d) introducing at least a portion of the first underflow stream to a second vibrating separator, to generate a second overflow stream and a second underflow stream, wherein the second overflow stream comprises biomass fragments; and
(e) combining at least some of the second overflow stream with the intermediate biomass stream from step (c), thereby generating clean biomass or optionally a clean biomass precursor stream that is shredded to provide clean biomass.

In some embodiments, the biomass feedstock is lignocellulosic biomass, such as sugarcane bagasse, sugarcane straw, energy cane bagasse, energy cane straw, corn stover, corn fiber, wheat straw, rice straw, oat straw, barley straw, miscanthus, or combinations thereof.

In some embodiments, the clean biomass contains at least 90% of the biomass content in the biomass feedstock. In these or other embodiments, the process removes at least 90% of grit contained in the biomass feedstock. Optionally, the second underflow stream may be combined with the large-grit stream, for disposal or other uses.

The clean biomass may be used in a wide variety of ways either in the biorefinery, in another plant, or in the market. The clean biomass may be stored for a period of time. For example, a batch of harvested biomass may be cleaned using the processes disclosed herein, and then the clean biomass may be employed as feedstock for a biorefining process over some other (e.g., longer) period of time.

The clean biomass may be further treated with one or more process steps selected from the group consisting of drying, size reduction, chemical pulping, mechanical pulping, steam explosion, hot-water extraction, acid-assisted extraction, base-assisted extraction, solvent-assisted delignification, acid-solvent fractionation, enzymatic hydrolysis, acid hydrolysis, base hydrolysis, pyrolysis, gasification, and combinations thereof.

The present invention also provides apparatus configured to carry out the processes disclosed. Some variations provide a biorefinery system including, or integrated with, the apparatus.

For example, some embodiments provide a system for cleaning biomass, the system comprising:

(a) a biomass feedstock inlet;
(b) a vibrating separator in operable communication with the biomass feedstock inlet, configured to generate an overflow stream and an underflow stream;
(c) a kinetic separator configured to separate the overflow stream into an intermediate biomass stream and a large-grit stream;
(d) a hydrocyclone separator configured to separate the underflow stream, with elutriation water, into a wet biomass-fines stream and a small-grit stream;
(e) a dewatering unit configured to remove water from the wet biomass-fines stream;
(f) a recycle line configured to recycle the water from the dewatering unit back to the hydrocyclone separator; and
(g) a mixer configured to combine the biomass fines stream from the dewatering unit with the intermediate biomass stream from the kinetic separator, thereby providing clean biomass.

Additionally, some variations provide a composition comprising clean biomass produced by a process as disclosed.

Figure 1:
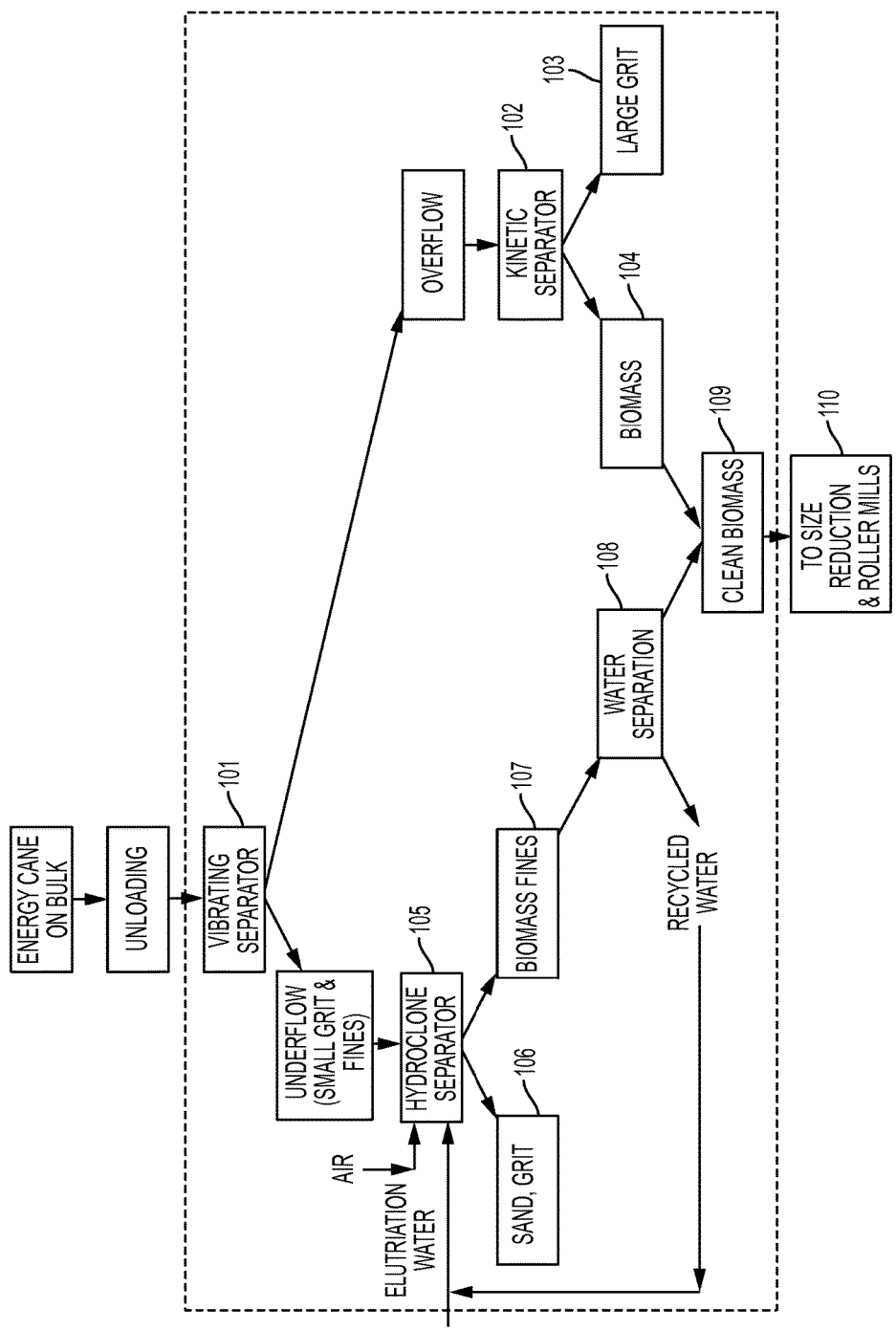
FIG. 1 is a block-flow diagram depicting some embodiments of the invention relating to wet cleaning of biomass.

These drawings are exemplary in nature and should not be construed to limit the invention in any way.

DETAILED DESCRIPTION OF SOME EMBODIMENTS

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. For example, reference to "unit" also includes a plurality of units (e.g., reactors or vessels). Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing parameters, reaction conditions, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Harvested biomass contains biomass and grits (minerals, sand, soil, etc). One purpose of removing foreign material like grit is to reduce abrasion and tear of the subsequent equipment processing the biomass.

In some variations, the invention provides a wet process for cleaning biomass, the process comprising:
  (a) providing biomass feedstock;
  (b) introducing the feedstock to a vibrating separator, to generate an overflow stream and an underflow stream, wherein the overflow stream comprises biomass and large grit, and wherein the underflow stream comprises fines and small grit;
  (c) introducing at least a portion of the overflow stream to a kinetic separator, to generate an intermediate biomass stream and a large-grit stream;
  (d) introducing at least a portion of the underflow stream and elutriation water to a hydrocyclone separator, to generate a wet biomass-fines stream and a small-grit stream;
  (e) separating at least some water contained in the wet biomass-fines stream and recycling the water to step (d) as at least some of the elutriation water, to generate a biomass fines stream; and
  (f) combining at least some of the biomass fines stream with the intermediate biomass stream from step (c), thereby generating clean biomass.

In some embodiments, the biomass feedstock is (or includes) lignocellulosic biomass. As used herein, "lignocellulosic biomass" means any material containing cellulose and lignin. Lignocellulosic biomass may also contain hemicellulose. Mixtures of one or more types of biomass can be used. In some embodiments, the biomass feedstock comprises both a lignocellulosic component (such as one described above) in addition to a sucrose-containing component (e.g., sugarcane or energy cane) and/or a starch component (e.g., corn, wheat, rice, etc.).

The biomass feedstock may be selected from hardwoods, softwoods, forest residues, industrial wastes, pulp and paper wastes, consumer wastes, or combinations thereof. Some embodiments utilize agricultural residues, which include lignocellulosic biomass associated with food crops, annual grasses, energy crops, or other annually renewable feedstocks. Exemplary agricultural residues include, but are not limited to, corn stover, corn fiber, wheat straw, sugarcane bagasse, sugarcane straw, rice straw, oat straw, barley straw, miscanthus, energy cane straw/residue, or combinations thereof. For example, the lignocellulosic biomass may be selected from the group consisting of sugarcane bagasse, sugarcane straw, energy cane bagasse, energy cane straw, corn stover, corn fiber, wheat straw, rice straw, oat straw, barley straw, miscanthus, and combinations thereof.

Various moisture levels may be associated with the starting biomass. The biomass feedstock need not be, but may be, relatively dry. In general, the biomass is in the form of a particulate or chip, but particle size is not critical in this invention.

The clean biomass preferably contains at least 90%, 91%, 92%, 93%, 94%, 95%, 96%, 97%, 98%, or 99% of the biomass content in the biomass feedstock. These values represent the recovery or yield of biomass, which for this calculation includes cellulose, hemicellulose, lignin, and other components (such as sugars, acids, proteins, silica, and metals) that are contained within the biomass structure itself.

The process preferably removes at least 90%, 91%, 92%, 93%, 94%, 95%, 96%, 97%, 98%, 99%, 99.5% or more of the grit contained in the biomass feedstock. As intended herein, "grit" includes sand, dirt, dust, foreign materials (i.e. materials that were not in the original biomass), and other generally non-organic, non-combustible particles. "Grit" does not include internal silica or minerals present in the biomass structure itself. In some washing embodiments, some amount of silica may be extracted out of biomass fibers, in addition to bulk grit removal.

Relatively low amounts of fresh water are necessary in step (d), since water is recycled from step (e) to function as elutriation water. In some embodiments, the process utilizes about or less than about 900, 800, 700, 600, 500, 400, 300, 250, 200, 150, 100, 90, 80, 70, 60, or 50 gallons of make-up water as elutriation water in step (d).

As used herein in some variations, biomass "fines" are defined as small particles passing through 200 mesh (or 76 μm in diameter) screen, according to Tappi 261 cm-10, which is incorporated by reference herein. These particles may include both cellulosic and non-cellulosic materials. The fines from annual plants are mostly originated from different small vessel elements such as tracheids, parenchyma cells, etc. and called "primary fines."

Vibrating separators are well-known, and any vibrating separator may be employed in step (b). In various embodiments, circle-throw vibrating separators, high-frequency vibrating separators, gyratory separators, chemical tumbler screeners, or rotating drums with trommel screens may be employed.

In certain embodiments, a vibratory screening device vibrates about its center of mass. Vibration is accomplished by eccentric weights on the upper and lower ends of the motion-generator shaft. Rotation of the top weight creates vibration in the horizontal plane, which causes material to move across the screen cloth to the periphery. The lower weight acts to tilt the machine, causing vibration in the vertical and tangential planes. The angle of lead given the lower weight with relation to the upper weight provides variable control of the spiral screening pattern. Speed and spiral pattern of material travel over the screen cloth can be set by the operator for maximum throughput and screening efficiency of the biomass feedstock.

Kinetic separators are also well-known. Generally, kinetic separators have no moving parts and are used to separate particles based on differences in specific gravity. In some embodiments, for example, a kinetic separator is based on the suspension of the materials in air, together with the kinetic effect of the biomass particles and grit in transit. The heavier grit is less affected by the physics and fall into a suitable and adjustable extraction gate. The injected air speed creates further dry cleaning of the biomass flow. The same air separates and transports all the fine particles and dust that are attached to the biomass.

Hydrocyclone separators are well-known. A hydrocyclone (often referred to in the shortened form cyclone) is a device to classify, separate, or sort particles in a liquid suspension (including elutriation water) based on the ratio of centripetal force to fluid resistance. This ratio is high for dense particles (where separation by density is desired) and coarse particles (where separation by size is desired), and low for light and fine particles. A hydrocyclone will normally have a cylindrical section at the top where liquid is being fed tangentially, and a conical base. The angle, and hence length of the conical section, plays a role in determining operating characteristics.

Step (e) may employ screens or other known separation means to recycle water back to step (d). In certain embodiments, a hydrocyclone with screen(s) may be used, such as to screen the liquid discharge.

Dispersers may also be added to liberate more biomass fines. A disperser may liberate additional fines that would not have otherwise been released. In some embodiments, a disperser is a simple mixing tank, i.e. a stirred tank or vessel. Dispersers may also be in-line (static) mixers, high-shear mixers, centrifuges, or other equipment. In some embodiments, the disperser is integrated with the classifier; for example, a centrifuge may be adapted to both disperse fines from solids as well as classify the fines as described above.

Some variations provide a two-step biomass cleaning system consisting of three modules, as depicted in FIG. 1. The first module entails a dry scalping which separates the incoming biomass into two streams of different grades, the reject or overflow of larger size particles and the material with smaller size going through the screen. The overflow fraction falls on a rotating kinetic separator which provides centrifugal acceleration producing different curving paths of the material in function of its density. This action allows for separating grit and clean biomass.

The second module corresponds to the separation of fine biomass from fine grit. This module is achieved through a wet separation in a sedimentation process with elutriation water and air bubbling. Elutriation water together with air provide buoyancy of the biomass fines without carrying small particle of grit. Separation follows the Stokes law. Grit is extracted from the bottom of the separator equipment and biomass fines are recovered at the top of the same separator.

The third module is the dewatering of the fine biomass. This is achieved by sending the stream from the separator on a vibrating dewatering shaker. Recovered water is recycled to the elutriation water stream and dewatered biomass fines are sent into the stream of clean biomass from the first module.

The process schematic in FIG. 1 will now be further described, without limitation of the scope of the invention.

The vibrating separator 101 is the first part of the first module. The equipment corresponds to a variable frequency vibrating screen. Important parameters to consider are frequency, amplitude of vibration, screen opening, screen opening direction and angle of incline deck will affect the unit output in term of capacity and separation efficiency.

The overflow falls into a kinetic separator 102 with variable drive revolutions to adjust for the separation efficiency of material with different densities. Large grits 103 and biomass 104 are separated.

The underflow from the vibrating separator 101 goes into a hydrocyclone separator 105 (e.g., hydraulic conical separator) where at the mid bottom air and elutriation water are injected. Grits 106 are removed from the bottom and the fines of biomass 107 are removed from the top of the hydrocyclone separator 105.

The biomass fines 107 are dewatered on a dewatering unit 108 (e.g., vibrating dewatering shaker) allowing to recover water which is recycled to the elutriation stream and dewatered biomass.

Dewatered biomass from dewatering unit 108 and biomass 104 together are referred to as "clean biomass stream" 109.

Stream 109 is then optionally sent to subsequent process, such as (without limitation) size reduction, roller mills, etc.

System advantages with respect to FIG. 1 may include biomass recovery over 97%, grit removal over 99%, and water usage about 100 gal per ton of removed grit, which is achieved with the combination of pressurized air with elutriation water.

Some embodiments provide a system for cleaning biomass, the system comprising:
 (a) a biomass feedstock inlet;
 (b) a vibrating separator in operable communication with the biomass feedstock inlet, configured to generate an overflow stream and an underflow stream;
 (c) a kinetic separator configured to separate the overflow stream into an intermediate biomass stream and a large-grit stream;
 (d) a hydrocyclone separator configured to separate the underflow stream, with elutriation water, into a wet biomass-fines stream and a small-grit stream;
 (e) a dewatering unit configured to remove water from the wet biomass-fines stream;
 (f) a recycle line configured to recycle the water from the dewatering unit back to the hydrocyclone separator; and (g) a mixer configured to combine the biomass fines stream from the dewatering unit with the intermediate biomass stream from the kinetic separator, thereby providing clean biomass.

In other variations of the invention, a dry process for cleaning biomass comprises:

(a) providing biomass feedstock;
(b) introducing the feedstock to a first vibrating separator, to generate a first overflow stream and a first underflow stream, wherein the first overflow stream comprises biomass and large grit, and wherein the first underflow stream comprises fines and small grit;
(c) introducing at least a portion of the first overflow stream to a kinetic separator, to generate an intermediate biomass stream and a large-grit stream;
(d) introducing at least a portion of the first underflow stream to a second vibrating separator, to generate a second overflow stream and a second underflow stream, wherein the second overflow stream comprises biomass fragments; and
(e) combining at least some of the second overflow stream with the intermediate biomass stream from step (c), thereby generating clean biomass or optionally a clean biomass precursor stream that is shredded to provide clean biomass.

Figure 2:
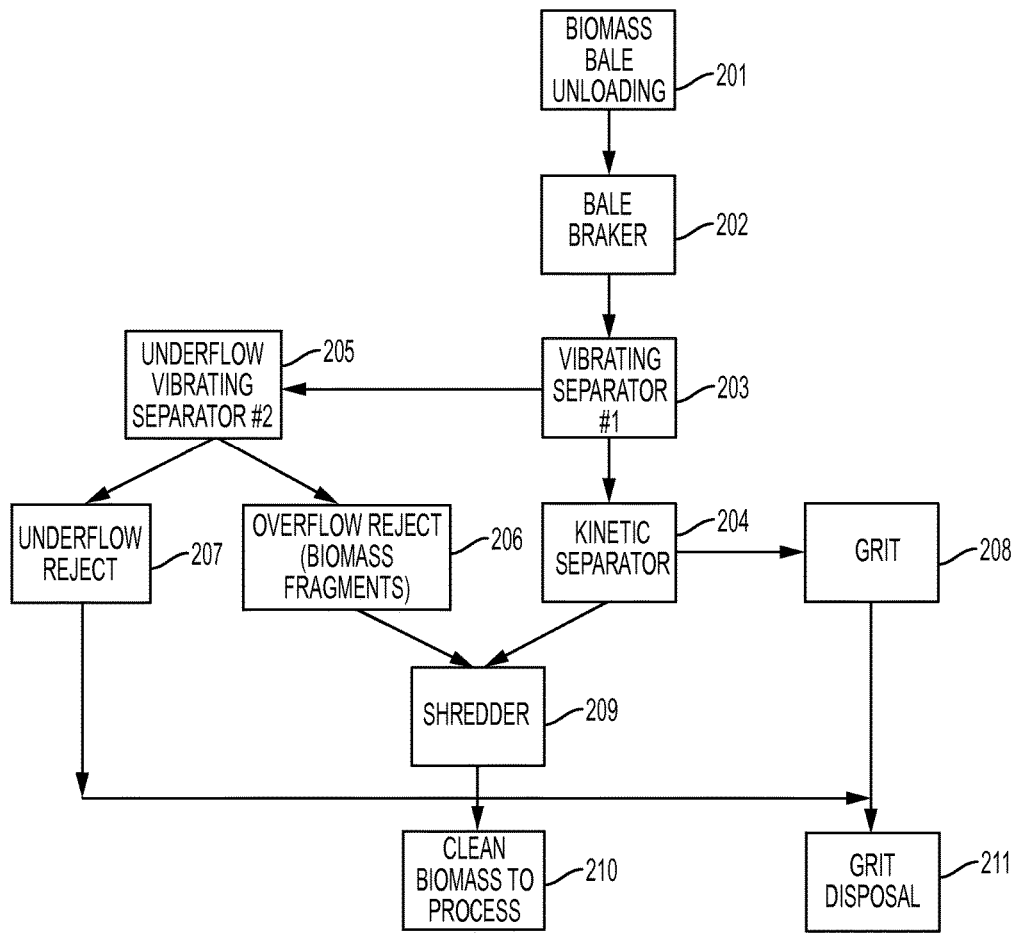
FIG. 2 is a block-flow diagram depicting some embodiments of the invention relating to dry cleaning of biomass.

FIG. 2 is a block-flow diagram depicting some embodiments of the invention relating to dry cleaning of biomass. Biomass bales may be unloaded 201 and broken 202. A first vibrating separator 203 generates a first overflow stream and a first underflow stream, wherein the first overflow stream comprises biomass and large grit, and wherein the first underflow stream comprises fines and small grit. A kinetic separator 204 receives the first overflow stream and separates it into an intermediate biomass stream and a large-grit stream 208. The first underflow stream is conveyed to a second vibrating separator 205, to generate a second overflow stream 206 and a second underflow stream 207, wherein the second overflow stream 206 comprises biomass fragments. The second underflow stream 207 is combined with grit 208 to grit disposal 211. A shredder 209 shreds the second overflow stream combined with the intermediate biomass stream from the kinetic separator 204. Clean biomass 210 is provided.

In some embodiments, the biomass feedstock is lignocellulosic biomass, such as sugarcane bagasse, sugarcane straw, energy cane bagasse, energy cane straw, corn stover, corn fiber, wheat straw, rice straw, oat straw, barley straw, miscanthus, or combinations thereof.

In some embodiments, the clean biomass contains at least 90% of the biomass content in the biomass feedstock. In these or other embodiments, the process removes at least 90% of grit contained in the biomass feedstock. Optionally, the second underflow stream may be combined with the large-grit stream, for disposal or other uses.

The clean biomass may be used in a wide variety of ways either in the biorefinery, in another plant, or in the market. The clean biomass may be stored for a period of time. For example, a batch of harvested biomass may be cleaned using the processes disclosed herein, and then the clean biomass may be employed as feedstock for a biorefining process over some other (e.g., longer) period of time.

The clean biomass may be further treated with one or more process steps selected from the group consisting of drying, size reduction, chemical pulping, mechanical pulping, steam explosion, hot-water extraction, acid-assisted extraction, base-assisted extraction, solvent-assisted delignification, acid-solvent fractionation, enzymatic hydrolysis, acid hydrolysis, base hydrolysis, pyrolysis, gasification, and combinations thereof.

The processes disclosed herein may be continuous, semi-continuous, or batch. In some embodiments, one or more steps are conducted countercurrently. In certain embodiments, the process is batch or semi-continuous, washing is conducted in simulated countercurrent fashion, and multiple wash streams (such as two, three, or more wash streams) are generated.

The present invention also provides apparatus configured to carry out the processes disclosed. Some variations provide a biorefinery system including, or integrated with, the apparatus. Additionally, some variations provide a composition comprising clean biomass produced by a process as disclosed.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A process for cleaning biomass, said process comprising:
   (a) providing biomass feedstock;
   (b) introducing said feedstock to a vibrating separator, to generate an overflow stream and an underflow stream, wherein said overflow stream comprises biomass and large grit, and wherein said underflow stream comprises fines and small grit;
   (c) introducing at least a portion of said overflow stream to a kinetic separator, to generate an intermediate biomass stream and a large-grit stream;
   (d) introducing at least a portion of said underflow stream and elutriation water to a hydrocyclone separator, to generate a wet biomass-fines stream and a small-grit stream;
   (e) separating at least some water contained in said wet biomass-fines stream and recycling said water to step (d) as at least some of said elutriation water, to generate a biomass fines stream; and
   (f) combining at least some of said biomass fines stream with said intermediate biomass stream from step (c), thereby generating clean biomass.

2. The process of claim 1, wherein said biomass feedstock is lignocellulosic biomass.

3. The process of claim 2, wherein said lignocellulosic biomass is selected from the group consisting of sugarcane bagasse, sugarcane straw, energy cane bagasse, energy cane straw, corn stover, corn fiber, wheat straw, rice straw, oat straw, barley straw, miscanthus, and combinations thereof.

4. The process of claim 1, wherein said clean biomass contains at least 95% of the biomass content in said biomass feedstock.

5. The process of claim 4, wherein said clean biomass contains at least 97% of the biomass content in said biomass feedstock.

6. The process of claim 1, wherein said process removes at least 90% of grit contained in said biomass feedstock.

7. The process of claim 6, wherein said process removes at least 95% of said grit contained in said biomass feedstock.

8. The process of claim 7, wherein said process removes at least 99% of said grit contained in said biomass feedstock.

9. The process of claim 1, wherein said process utilizes about 500 gallons of make-up water, or less, as said elutriation water in step (d).

10. The process of claim 9, wherein said process utilizes about 200 gallons of said make-up water, or less, as said elutriation water in step (d).

11. The process of claim 10, wherein said process utilizes about 100 gallons of said make-up water, or less, as said elutriation water in step (d).

12. The process of claim 1, wherein said clean biomass is further treated with one or more process steps selected from the group consisting of drying, size reduction, chemical pulping, mechanical pulping, steam explosion, hot-water extraction, acid-assisted extraction, base-assisted extraction, solvent-assisted delignification, acid-solvent fractionation, enzymatic hydrolysis, acid hydrolysis, base hydrolysis, pyrolysis, gasification, and combinations thereof.

* * * * *